United States Patent [19]

Horie et al.

[11] Patent Number: 4,853,262

[45] Date of Patent: Aug. 1, 1989

[54] COVER FILM FOR MICROSCOPY

[75] Inventors: Ikutaro Horie; Masashi Ishiyama; Teiichi Tomizuka, all of Minami-ashigara, Japan

[73] Assignee: Fuji Photo Film Co., Ltd., Minami-ashigara, Japan

[21] Appl. No.: 895,665

[22] Filed: Aug. 11, 1986

[30] Foreign Application Priority Data

Aug. 13, 1985 [JP] Japan .................. 60-178327

[51] Int. Cl.$^4$ ............... G01N 1/28; G02B 21/34; C09J 7/02
[52] U.S. Cl. .................. 428/13; 428/34; 428/38; 428/346; 156/57; 424/3
[58] Field of Search ............ 428/13, 34, 38, 346; 156/57; 424/3

[56] References Cited

U.S. PATENT DOCUMENTS

| | | | |
|---|---|---|---|
| 3,498,860 | 8/1965 | Pickett | 156/57 |
| 3,891,327 | 6/1975 | Welch | 424/3 X |
| 3,939,019 | 2/1976 | Pickett | 156/57 |
| 4,146,414 | 3/1979 | Stormby | 424/3 X |
| 4,188,246 | 2/1980 | Lipshaw | 156/57 |
| 4,302,480 | 11/1981 | Fischer et al. | 156/57 X |
| 4,320,157 | 3/1982 | von Hagens | 428/13 |
| 4,463,117 | 7/1984 | Malin | 156/57 X |
| 4,545,831 | 10/1985 | Ornstein | 156/57 |
| 4,588,579 | 5/1986 | Bachhuber et al. | 424/3 |
| 4,621,009 | 11/1986 | Lad | 428/480 X |

OTHER PUBLICATIONS

"Preparation of Copolymers of Isobutyl Methacrylate and Styrene for Mounting Media", Grant, Stain Technology, vol. 25, No. 2, Apr. (1950).

*Primary Examiner*—George F. Lesmes
*Assistant Examiner*—M. A. Katz
*Attorney, Agent, or Firm*—Burns, Doane, Swecker & Mathis

[57] ABSTRACT

A cover film for use in microscopy which has an excellent adhesion with a slide glass and does not cause blocking during storage is obtained by coating a solution of a polymer adhesive having a glass transition temperature of at least 50° C. in an organic solvent on a transparent substrate and evaporating the organic solvent.

10 Claims, No Drawings

COVER FILM FOR MICROSCOPY

FIELD OF THE INVENTION

The present invention relates to a cover film suitable to automatic sealing for use in microscopy.

BACKGROUND OF THE INVENTION

In examination by a microscope, a subject to be examined is sandwiched with a cover glass and a slide glass, which is then placed with the cover glass facing an object lens. However, the mere sandwiching of a subject to be examined with two glass plates often does not allow later examination of the same subject. In order to solve this problem, an adhesive was proposed. This is called a sealing agent and is used to sandwich a slice of an observed object, having dimensions of micron order, between two glass plates and pressure it in the same state as examined so that it can be stored for an extended period.

One of well known sealing agents is Balsam. This is a natural product and, therefore, has a disadvantage that its composition and quality vary depending on a growing district, a degree of purification, preservation conditions, etc. For the above reason, synthetic polymeric adhesives have been tried as sealing agents. See, for instance, Taichiro Akiyama and Setsuko Ueno, Rinshokensa, November 1966.

An increasing number of subjects are subjected to microscopic examination in the fields of medical science, pharmacology, biology, agricultural science and technology.

Operation of filling an interstice between two glass plates with a thin sealing agent layer to fix them is conducted almost completely manually. However, it is becoming impossible with such manual operation to meet the increasing quantity and time demands. In order to solve this problem, a method of automatically preparing specimens for microscopic examination was proposed as seen in U.S. Pat. Nos. 4,146,414 and 4,203,797, wherein a film composed of a transparent substrate coated with an adhesive is automatically layered on a slide glass on which a few drops of an organic solvent, capable of swelling or dissolving the above adhesive, has previously been dropped and a subject to be examined has been placed. Thus, the aforesaid film has both the function of a traditional cover glass and the function of a sealing agent. This type of film is hereinafter called a cover film.

However, this cover film of a transparent substrate previously coated with an adhesive requires improvement to permit a user to stably use it any time and anywhere. That is, the cover film easily causes so-called blocking between an adhesive layer and the reverse side of the film, i.e., the substrate surface opposite to the adhesive layer, during storage in a form of a roll. Once the blocking occurs, the adhesive layer transfers to the reverse side of the film or the surface of the adhesive layer becomes uneven, so that satisfactory sealing required for microscopic examination is unattainable.

Further, a sealed specimen for microscopic examination is not always stored at normal temperature and humidity. Some countermeasure is, therefore, required to prevent peeling-off between the cover film and the slide glass or between the substrate of the cover film and the sealing agent layer, even if it is stored in a certain range of temperature and humidity.

SUMMARY OF THE INVENTION

One purpose of the invention is to find a synthetic polymer adhesive suitable as a sealing agent.

Another purpose of the invention is to provide a cover film which does not cause blocking and adheres quickly when contacted with only a small amount of an organic solvent.

The other purpose of the invention is to provide a cover film which does not cause peeling-off between the cover film and the slide glass or between the substrate of the cover film and the sealing agent layer even when the sealed specimen for microscopic examination is stored at a low temperature such as $-20°$ C. or a relatively high temperature such as $+40°$ C., or at a low humidity such as 10% relative humidity (R.H.) or at a high humidity such as 80% R.H.

It has now been found that the above purposes are attained by a film obtained by coating a polymer adhesive having a glass transition temperature of at least 50° C. on a transparent substrate. The polymer adhesive is dissolved in an organic solvent, coated on a substrate, and then the solvent is evaporated.

DETAILED DESCRIPTION OF THE INVENTION

The polymer adhesive preferably dissolves in an organic solvent used in an automatic sealing unit or, at least, has to swell in the above solvent. It is preferred that the adhesive is soluble in any one of xylene, toluene, ethyl acetate, methyl acetate, acetone and methyl ethyl ketone alone or in a mixed solvent of two or more of these. There are many polymer adhesives which have a glass transition temperature of at least 50° C. and are soluble in the above solvent. Such polymer adhesives commercially available include a polyester adhesive, such as the thermoplastic polyester adhesive Vylon 200 (Trademark, Toyo Boseki Co., Japan), acrylic adhesives, Aron S-1017, S-1030C (Trademark, Toagosei Kagaku, Japan). For calculation of a glass transition temperature of a copolymer composed of two monomers, Fox's equation is known (Seizo Okamura et al., Kobunshikagaku Joron, 2nd ed., p. 172, Kagaku Dojin).

$$\frac{1}{T_g + 273} = \frac{W_1}{T_{g1} + 273} + \frac{W_2}{T_{g2} + 273}$$

$$W_1 + W_2 = 1$$

where
  $T_g$=glass transition temperature of copolymer (°C.),
  $T_{g1}$=glass transition temperature of homopolymer of one monomer (°C.),
  $W_1$=weight ratio of one monomer,
  $T_{g2}$=glass transition temperature of homopolymer of the other monomer (°C.), and
  $W_2$=weight ratio of the other monomer.

The values of glass transition temperatures of various homopolymers are shown in J. Brandrup and E. H. Immergut, ed., Polymer Handbook, 2nd ed., John Wiley & Sons.

Taking an acrylic copolymer composed of methyl methacrylate and butyl methacrylate as one example,

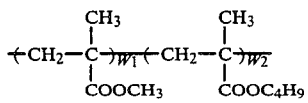

$Tg_1 = 105$, $Tg_2 = 20$, accordingly, $W_1$ and $W_2$ which give $T_g$ equal to or higher than 50 are obtained from Fox's equation: $W_1 \geq 0.4$ and $W_2 \leq 0.6$, approximately.

In the case where the monomer components are methyl methacrylate and methyl acrylate, similarly

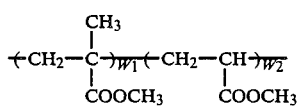

$Tg_1 = 105$, $Tg_2 = 10$, accordingly, $W_1 \geq 0.5$ and $W_2 \leq 0.5$, approximately, for $Tg \geq 50$.

The glass transition temperature of a copolymer used in the present invention is calculated according to the above method of calculation. The glass transition temperature of a copolymer composed of three or more comonomers can be calculated in a similar way.

A preferred acrylic adhesive is a copolymer of alkyl methacrylate and alkyl acrylate.

U.S. Pat. No. 3,498,860 discloses that a cover glass is previously coated with an acrylic polymer adhesive, which is then dissolved by xylene or toluene to bond the cover glass to a slide glass. However, this patent does not suggest at all that a polymer adhesive having a glass transition temperature of at least 50° C. is effective to prevent blocking. This has been found by the present inventors for the first time.

Further, it is preferred that a film of the polymer adhesive has a refractive index, $\eta_D$, of at least 1.45, more preferably at least 1.47, which lessens optical difficulties in microscopic examination.

These polymer adhesives may be used for coating alone or in combination as a blend. When a blend of adhesives is used, a blend ratio should be chosen so that a film after evaporation of an organic solvent shows no opaqueness.

The coated amount of the polymer adhesive layer after evaporation of an organic solvent is preferably in a range of from 1 g/m² to 50 g/m², more preferably a range of from 7 g/m² to 25 g/m².

In a preferred embodiment of blending the adhesives, a polymer adhesive, for instance acrylic polymer adhesive, of a glass transition temperature of at least 80° C. and another polymer adhesive, for instance acrylic polymer adhesive, of a glass transition temperature of 50° C. or higher but lower than 80° C. are blended in a weight ratio of 7:3 to 5:5.

For a cover film, a transparent substrate coated with the above polymer adhesive may attain the present purposes in almost all cases. However, it is also possible to provide a protective layer on the adhesive layer by coating or to provide a backing layer on the reverse side of the substrate (i.e., reverse to the adhesive layer) by coating in order to prevent scratching on the adhesive surface and/or the substrate surface, to more surely prevent the blocking during storage at a very high temperature and to keep curling balance. Synthetic polymers having a high glass transition temperature, such as polystyrene and polymethyl methacrylate, and gelatine may be used as a constructive material of the protective layer or the backing layer.

All of the substances known as a transparent substrate may almost attain the purpose of the invention. Preferred examples are films of cellulose triacetate, cellulose diacetate and polyethylene terephthalate.

The thickness of the substrate is preferably in a range of from 50μ to 250μ, more preferably from 100μ to 150μ. The substrate may be provided with a subbing layer well known in the photographic material industry by coating or subjected to surface treatment by ultraviolet radiation, corona discharge or glow discharge.

The cover film for microscopy according to the invention has an advantage that blocking is not caused during storage in a roll form in a range of low to high temperatures and low to high humidities. In addition, the cover film has has the excellent functions required for a cover film. That is, it adheres quickly when contacted with an organic solvent and does not peel off.

The invention will further be explained in the examples below.

EXAMPLE 1

Aron S-1017 (glass transition temperature 87° C., Toagosei Kagaku, Japan) or Aron S-1015 (glass transition temperature 21° C., Toagosei Kagaku, Japan) dissolved in a mixed solvent of ethyl acetate and toluene in 1:1 (volume ratio) was applied on a cellulose triacetate substrate and a cellulose diacetate substrate, both of which are transparent and 135μ in thickness, and dried to yield the samples shown in Table 1.

TABLE 1

| Sample | Transparent Substrate | Sealing Agent | Solid Content in Sealing Agent Layer (g/m²) | |
|---|---|---|---|---|
| a | Cellulose triacetate | Aron S-1017 | 22 | Invention |
| b | " | Aron S-1015 | 22 | Comparison |
| c | Cellulose diacetate | Aron S-1017 | 22 | Invention |
| d | " | Aron S-1015 | 22 | Comparison |

The above samples were slit to a 24 mm width and 60 m of each of them were wound on a winding core of 126 mm in diameter in such a manner that the sealing agent layer faced the winding core. The wound samples were put together with (bound to) slide glasses using Coveraid automatic sealing unit SCA-1800 (Sakura Seiki Co., Japan) to evaluate an adhering property. The results are shown in Table 2.

TABLE 2

| Sample | Evaluation Adhering Property (After 1 Hour Storage at Room Temp.) |
|---|---|
| a | 3 |
| b | 3 |
| c | 3 |
| d | 3 |

Rate for evaluation of adhering property:
1: Not adhere. Peels off of itself.
2: Adheres, but slides with a rub by a finger.
3: Adheres strongly so as not to slide with a rub by a finger.

Meanwhile, the above wound samples were stored at 60° C. and 50% R.H. for 7 days and evaluated for blocking. The results are shown in Table 3.

TABLE 3

| Sample | Evaluation of Blocking |
|---|---|
| a | No blocking at all |
| b | Blocking on almost all surface |
| c | No blocking at all |
| d | Blocking on almost all surface |

It is seen from Table 2 and 3 that a cover film coated with a polymer adhesive having a high glass temperature has an excellent adhesion with a slide glass and does not easily cause blocking during storage.

EXAMPLE 2

Vylon 200 (glass transition temperature 67° C. or Vylon 300 (glass transition temperature 7° C., both sold by Toyo Boseki Co., Japan) dissolved in ethyl acetate was applied on a transparent cellulose triacetate substrate of 150$\mu$ in thickness, and dried to yield the samples shown in Table 4.

TABLE 4

| Sample | Sealing Agent | Solid Content in Sealing Agent Layer (g/m$^2$) | |
|---|---|---|---|
| a | Vylon 200 | 2.0 | Invention |
| b | " | 7.5 | " |
| c | " | 15 | " |
| d | Vylon 300 | 2.0 | Comparison |
| e | " | 7.5 | " |
| f | " | 15 | " |

These were put together with slide glasses as in Example 1 and evaluated for their adhering properties. The results are shown in Table 5.

TABLE 5

| Sample | Evaluation of Adhering Property (After 5 Hours Storage at Room Temp.) |
|---|---|
| a | 2 |
| b | 3 |
| c | 3 |
| d | 2 |
| e | 3 |
| f | 3 |

Meanwhile, the wound samples were stored at 40° C. and 80% R.H. for 3 days and evaluated for blocking. The results are shown in Table 6.

TABLE 6

| Sample | Evaluation of Blocking |
|---|---|
| a | Almost no blocking |
| b | " |
| c | " |
| d | Blocking on almost all surface |
| e | " |
| f | " |

It is seen from Tables 5 and 6 that a cover film coated with a polymer adhesive having a high glass transition temperature has an excellent adhesion with a slide glass and does not easily cause blocking during storage.

EXAMPLE 3

Vylon 500 (glass transition temperature 4° C.), Vylon 103 (glass transition temperature 47° C.) or Vylon 200 (glass transition temperature 67° C., all sold by Toyo Boseki Co., Japan) dissolved in a mixed solvent of toluene and methyl ethyl ketone in 8:2 (by volume) was applied on a transparent polyethylene terephthalate substrate of 80$\mu$ in thickness, and dried to yield the samples shown in Table 7.

TABLE 7

| Sample | Sealing Agent | Solid Content in Sealing Agent Layer (g/m$^2$) | |
|---|---|---|---|
| a | Vylon 500 | 10 | Comparison |
| b | Vylon 103 | 10 | Comparison |
| c | Vylon 200 | 10 | Invention |

These were put together with slide glasses as in Example 1 and evaluated for an adhering property, which results are shown in Table 8.

TABLE 8

| Sample | Evaluation of Adhering Property (After 1 Day Storage at Room Temp.) |
|---|---|
| a | 3 |
| b | 3 |
| c | 3 |

Meanwhile, the wound samples were stored at 30° C. and 60% R.H. for 5 days and evaluated for blocking, which results are shown in Table 9.

TABLE 9

| Sample | Evaluation of Blocking |
|---|---|
| a | Blocking on almost all surface |
| b | Blocking on half the surface |
| c | No blocking at all |

It is seen from Tables 8 and 9 that a cover film coated with a polymer adhesive having a high glass transition temperature has an excellent adhesion with a slide glass and does not easily cause blocking during storage.

EXAMPLE 4

A blend of Aron S-1017 (glass transition temperature 87° C.) and Aron S-1030C (glass transition temperature 52° C., both sold by Toagosei Kagaku Co.) dissolved in a mixed solvent of acetone and toluene in 6:4 (by volume) was applied on a transparent polyethylene terephthalate substrate of 100$\mu$ in thickness, and dried to yield the samples shown in Table 10.

TABLE 10

| Sample | Blending Ratio of Aron S-1017 to Aron S-1030C (weight ratio) | Solid Content in Sealing Agent Layer (g/m$^2$) |
|---|---|---|
| a | 7:3 | 15 |
| b | 6:4 | 15 |
| c | 5:5 | 15 |
| d | 4:6 | 15 |

The above samples were put together with slide glasses and evaluated for an adhering property, which results are shown in Table 11.

TABLE 11

| Sample | Evaluation of Adhering Property (After 1 Hour Storage at Room Temp.) |
|---|---|
| a | 3 |
| b | 3 |
| c | 3 |
| d | 3 |

Meanwhile, the cover films being put together with slide glasses were stored in various conditions and evaluated again for an adhering property, which results are shown in Table 12.

TABLE 12

| | Evaluation of Adhering Property Storage Conditions | | | |
|---|---|---|---|---|
| Sample | −20° C. 7 days | 25° C., 40% R.H. 7 days | 35° C., 80% R.H. 7 days | 60° C., 40% R.H. 7 days |
| a | 3 | 3 | 3 | 3 |
| b | 3 | 3 | 3 | 3 |
| c | 3 | 3 | 3 | 3 |
| d | 3 | 3 | 3 | 3 |

The wound samples were stored at 45° C. and 80% R.H. for 7 days and evaluated for blocking, which results are shown in Table 13.

TABLE 13

| Sample | Evaluation of Blocking |
|---|---|
| a | No blocking at all |
| b | No blocking at all |
| c | No blocking at all |
| d | Almost no blocking |

It is seen from Tables 11, 12 and 13 that, when polymer adhesives having a glass transition temperature of 50° C. or higher are respectively, blended, it is also possible to obtain a cover film which shows an excellent sealing property and does not easily cause blocking.

What is claimed is:

1. A cover film for use in microscopy, which comprises a transparent plastic substrate having provided thereon a layer of a polymer adhesive which is a blend of a first polymer adhesive and second polymer adhesive which are different and which are both selected from the group consisting of an acrylic adhesive and an acrylic copolymer of alkyl methacrylate and alkyl acrylate, said first polymer adhesive having a glass transition temperature of at least 80° C. and said second polymer adhesive having a glass transition temperature of 50° C. to less than 80° C. with the weight ratio of the first adhesive to the second adhesive being 7:3 to 5:5 and said polymer adhesive being soluble in any one of xylene, toluene, ethyl acetate, methyl acetate, acetone, methyl ethyl ketone or mixtures thereof.

2. The cover film of claim 1, wherein said polymer adhesive has a refractive index of at least 1.45.

3. The cover film of claim 2, wherein said polymer adhesive has a refractive index of at least 1.47.

4. The cover film of claim 1, wherein said polymer adhesive is coated in an amount of 1 to 50 g/m$^2$ after drying.

5. The cover film of claim 4, wherein said polymer adhesive is coated in an amount of 7 to 25 g/m$^2$ after drying.

6. The cover film of claim 1, wherein said first and second polymer adhesives are acrylic polymer adhesives.

7. The cover film of claim 1, wherein a protective layer is provided on said adhesive layer.

8. The cover film of claim 1, wherein a backing layer is provided on the reverse side of the substrate.

9. The cover film of claim 1, wherein said substrate is selected from the group consisting of cellulose triacetate, cellulose diacetate and polyethylene terephthalate films.

10. The cover film of claim 1, wherein said substrate has thickness of 50 to 250 microns.

* * * * *